United States Patent
Hoffman

(10) Patent No.: US 12,157,017 B2
(45) Date of Patent: Dec. 3, 2024

(54) PERSONAL USE EXTRACORPOREAL LOW INTENSITY SHOCK WAVE DEVICE ENHANCED USER FEATURES AND FUNCTIONS

(71) Applicant: MOON POOL LLC, Chatsworth, CA (US)

(72) Inventor: Jonathan Hoffman, Studio City, CA (US)

(73) Assignee: MOON POOL LLC, Chatsworth, CA (US)

( * ) Notice: Subject to any disclaimer, the term of this patent is extended or adjusted under 35 U.S.C. 154(b) by 18 days.

(21) Appl. No.: 18/062,796

(22) Filed: Dec. 7, 2022

(65) Prior Publication Data
US 2023/0094456 A1 Mar. 30, 2023

Related U.S. Application Data

(63) Continuation of application No. 16/850,885, filed on Apr. 16, 2020, now Pat. No. 11,547,875.

(60) Provisional application No. 62/903,926, filed on Sep. 22, 2019.

(51) Int. Cl.
*A61N 7/00* (2006.01)

(52) U.S. Cl.
CPC ........ *A61N 7/00* (2013.01); *A61N 2007/0017* (2013.01); *A61N 2007/0034* (2013.01)

(58) Field of Classification Search
CPC .............. A61N 7/00; A61N 2007/0017; A61N 2007/0034; A61B 90/361
See application file for complete search history.

(56) References Cited

U.S. PATENT DOCUMENTS

| | | |
|---|---|---|
| 6,217,531 B1 | 4/2001 | Reitmajer |
| 7,390,308 B2 | 6/2008 | Schultheiss |
| 7,470,240 B2 | 12/2008 | Schultheiss et al. |
| 7,497,834 B2 | 3/2009 | Schaden et al. |
| 7,497,835 B2 | 3/2009 | Schultheiss et al. |
| 7,497,836 B2 | 3/2009 | Schultheiss et al. |
| 7,507,213 B2 | 3/2009 | Schultheiss et al. |
| 7,537,572 B2 | 5/2009 | Schultheiss et al. |
| 7,544,171 B2 | 6/2009 | Schaden et al. |
| 7,578,796 B2 | 8/2009 | Schultheiss et al. |
| 7,594,930 B2 | 9/2009 | Warlick et al. |
| 7,600,343 B2 | 10/2009 | Schultheiss et al. |
| 7,601,127 B2 | 10/2009 | Schultheiss et al. |
| 7,695,443 B2 | 4/2010 | Voss |

(Continued)

FOREIGN PATENT DOCUMENTS

| | | |
|---|---|---|
| WO | 2007087470 A2 | 8/2007 |
| WO | 2007098300 A2 | 8/2007 |

*Primary Examiner* — Hien N Nguyen
(74) *Attorney, Agent, or Firm* — SLEMAN & LUND LLP

(57) ABSTRACT

A device which utilizes low intensity extracorporeal shock therapy for purposes of treating soft tissue damage, cellulite reduction, or erectile dysfunction, to permit a simple, inexpensive, robust, home use solution which permits self-applied treatment for various parts of the user's body with a form factor, display, information, guidance, tutorials and training, marketing communication and purchase opportunities, viewing angle, timers, annunciators, sound attenuation, and payment options which provide an untrained amateur user with all tools and guidance necessary to properly, effectively, safely and affordably self-administer treatments.

15 Claims, 4 Drawing Sheets

(56) References Cited

U.S. PATENT DOCUMENTS

| | | |
|---|---|---|
| 7,775,995 B2 | 8/2010 | Voss |
| 7,841,995 B2 | 11/2010 | Schultheiss et al. |
| 7,883,482 B2 | 2/2011 | Schultheiss et al. |
| 7,905,845 B2 | 3/2011 | Schultheiss et al. |
| 7,988,648 B2 | 8/2011 | Warlick et al. |
| 8,162,859 B2 | 4/2012 | Schultheiss et al. |
| 8,197,444 B1* | 6/2012 | Bazargan .......... A61M 5/16854 604/131 |
| 8,257,282 B2 | 9/2012 | Uebelacker et al. |
| 8,535,249 B2 | 9/2013 | Uebelacker et al. |
| 10,716,565 B2 | 7/2020 | Shelton, IV et al. |
| 2007/0053795 A1* | 3/2007 | Laugharn, Jr. .......... B01F 31/87 73/644 |
| 2007/0239082 A1 | 10/2007 | Schultheiss et al. |
| 2008/0183111 A1 | 7/2008 | Voss |
| 2008/0191596 A1 | 8/2008 | King |
| 2008/0269651 A1 | 10/2008 | Warlick et al. |
| 2009/0041864 A1 | 2/2009 | Warlick |
| 2009/0088670 A1 | 4/2009 | Warlick et al. |
| 2009/0093739 A1 | 4/2009 | Voss |
| 2009/0221940 A1 | 9/2009 | Marlinghaus et al. |
| 2010/0113966 A1 | 5/2010 | Spruce |
| 2011/0130714 A1* | 6/2011 | Wells ...................... A61M 1/77 604/28 |
| 2011/0177576 A1 | 7/2011 | Schaden et al. |
| 2012/0226268 A1* | 9/2012 | Liu ...................... A61N 5/0613 606/9 |
| 2013/0231735 A1* | 9/2013 | Deem .................. A61F 2/2436 623/2.11 |
| 2014/0350438 A1* | 11/2014 | Papirov .................. A61N 7/00 601/2 |
| 2015/0133950 A1 | 5/2015 | Shelton et al. |
| 2016/0022352 A1* | 1/2016 | Johnson ................ A61B 18/14 606/41 |
| 2017/0296185 A1 | 10/2017 | Swensgard et al. |
| 2020/0397935 A1* | 12/2020 | Church ................ G06F 3/0482 |
| 2021/0307845 A1 | 10/2021 | Park et al. |

\* cited by examiner

PERSONAL USE EXTRACORPOREAL LOW INTENSITY SHOCK WAVE DEVICE ENHANCED USER FEATURES AND FUNCTIONS

CROSS-REFERENCE TO RELATED APPLICATIONS

The present application is a continuation of U.S. application Ser. No. 16/850,885, filed Apr. 16, 2020, entitled "PERSONAL USE EXTRACORPOREAL LOW INTENSITY SHOCK WAVE DEVICE ENHANCED USER FEATURES AND FUNCTIONS," which claims the benefit of U.S. Provisional Application Ser. No. 62/903,926, filed Sep. 22, 2019, entitled "PERSONAL USE EXTRACORPOREAL LOW INTENSITY SHOCK WAVE DEVICE ENHANCED USER FEATURES AND FUNCTIONS," the contents of which are hereby incorporated by reference as if fully set forth herein.

FIELD OF THE DISCLOSURE

The present disclosure relates to non-invasive home use low intensity shock wave therapy medical devices. More specifically, the present disclosure relates to non-invasive home use low intensity shock wave therapy medical devices for, for example, treating erectile dysfunction or removing cellulite.

BACKGROUND OF THE DISCLOSURE

Low intensity extracorporeal shock wave treatments are well known in the art and have been widely known and used in the professional medical community for several decades. The treatment methodology has been demonstrated to be effective in treating soft tissue injuries or damage, reducing fatty deposits commonly known as cellulite, and most recently for the treatment of male erectile dysfunction.

Conventional devices are intended to be utilized by a trained, skilled professional applying the treatment to a third-party patient or subject. Such devices require specific knowledge about human anatomy, treatment protocol and regimen, rate of travel of device, pressure to be applied by device, duration of treatment, and frequency of treatment. Further, the controls and displays of such devices are so positioned as to be visible and accessible to a third-party professional treatment specialist, not to a self-user. Further the cost of such devices may be prohibitively high, rendering the purchase or use of such devices beyond the means of the average user.

SUMMARY OF THE DISCLOSURE

In at least some examples, a treatment device includes a housing having a longitudinal axis extending between a proximal end and a distal end, a striking element disposed within the housing and moveable along the longitudinal axis, a tip disposed adjacent the distal end, and a position indicator for alerting the user to a proper location on the body to be treated.

In at least some examples, a treatment device includes a housing having a longitudinal axis extending between a proximal end and a distal end, a striking element disposed within the housing and moveable along the longitudinal axis, a tip disposed adjacent the distal end, a processor and a memory.

In at least some examples, a treatment device includes a housing having a longitudinal axis extending between a proximal end and a distal end, a striking element disposed within the housing and moveable along the longitudinal axis, a tip disposed adjacent the distal end, and a speed indicator.

BRIEF DESCRIPTION OF DRAWINGS

Various embodiments of the presently disclosed treatment devices are disclosed herein with reference to the drawings, wherein.

Figure 1:
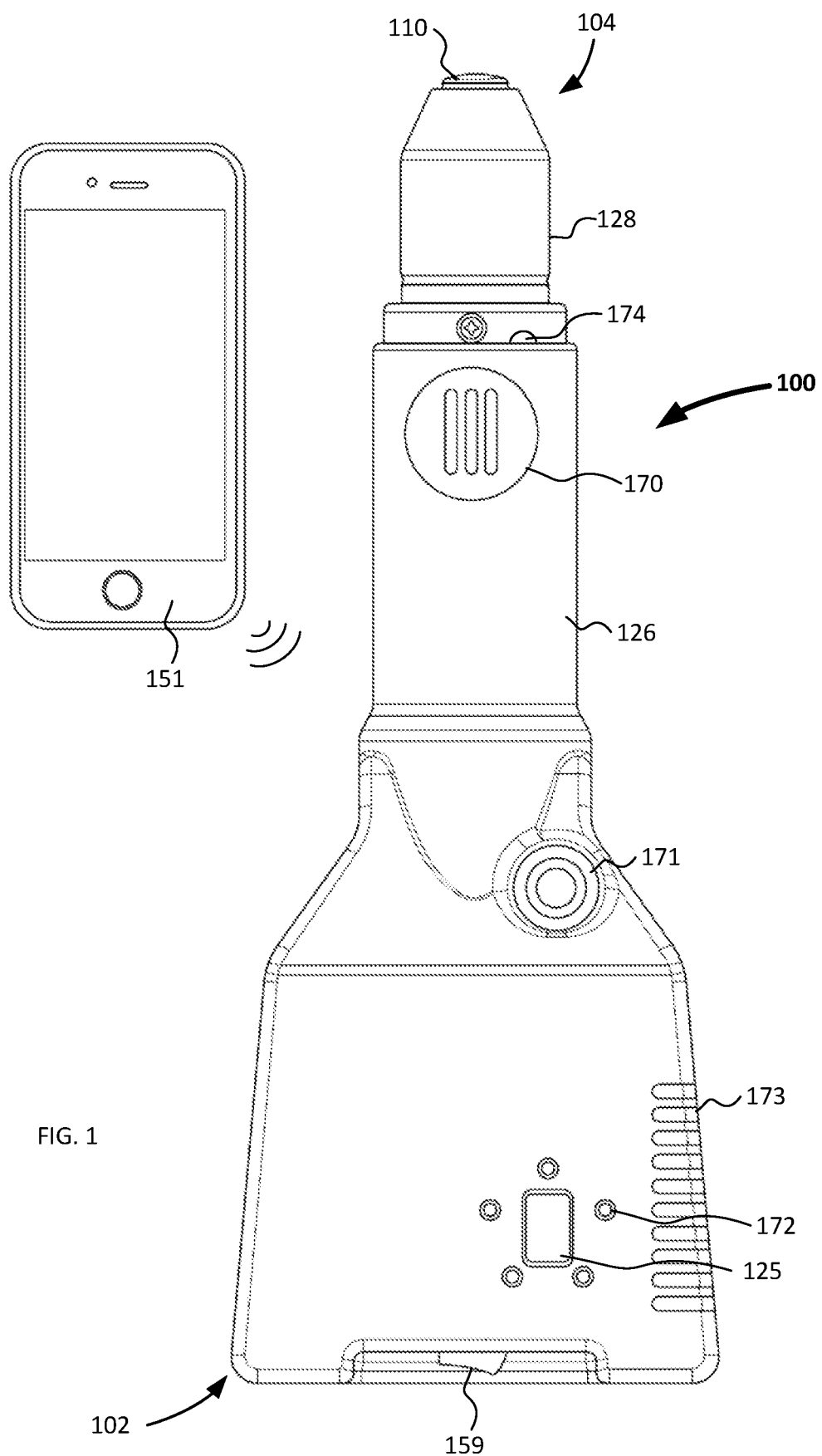
FIG. 1 shows a schematic plan view of one embodiment of the disclosure.

Various embodiments of the present disclosure will now be described with reference to the appended drawings. It is to be appreciated that these drawings depict only some embodiments of the disclosure and are therefore not to be considered limiting of its scope.

DETAILED DESCRIPTION

Despite the various improvements that have been made to acoustic wave treatment devices, conventional devices suffer from some shortcomings.

There therefore is a need for further improvements to the devices, systems, and methods of manufacturing and using acoustic wave treatment devices. Among other advantages, the present disclosure may address one or more of these needs.

As used herein, the term "proximal," when used in connection with a component of a treatment device, refers to the end of the component farthest from the treatment area, whereas the term "distal," when used in connection with a component of a treatment, refers to the end of the component closest to the treatment area.

Likewise, the terms "trailing" and "leading" are to be taken as relative to the operator of the treatment device. "Trailing" is to be understood as relatively closer to the operator, and "leading" is to be understood as relatively farther away from the operator or closer to the target site of treatment.

In conjunction with the included drawings, this detailed description is intended to impart an understanding of the teachings herein and not to define their metes and bounds. One particular implementation, illustrating aspects of the present teaching, is presented in detail below. Some of the many possible variations and versions are also described.

Conventional devices generally have a form factor that is intended for a professional medical provider to administer treatment to a third-party subject or patient and as such is not ergonomically well suited for an individual to self-administer treatment. Additionally, there are no displays and controls that are readily visible or accessible to an individual self-administering treatment. Conventional devices also do not provide any information regarding proper positioning of the device during treatment to assist an untrained user in the proper positioning of the device during use.

In contrast, the present disclosure contemplates devices capable of providing information regarding proper rate of travel of the device during treatment to assist an untrained user in the proper movement of the device during use. The present devices and methods also provide information regarding the number of passes completed at any given time of the device during treatment to assist an untrained user in the proper duration of treatment of the device during use. The present device and methods also monitor and/or limit the operating time of the device during treatment to assist an untrained user in avoiding over-treatment of the device. For example, the proposed methods and devices may include monitoring and/or limiting of the total number of operating cycles of the device to assist an untrained user in understanding the operational service life, and need for periodic maintenance of the device.

The present devices and methods address problems with the limited viewing angle of the information display of the device which is detrimental to a self-administering user who must hold the device in a variety of positions and orientations during use, while still needing to see the displayed information during use. The also address problems associated with significant decibel levels of sound produced by the device during use which alerts others in proximity to the user that the device is in use and thereby prevents the discreet use of the device such as may be desired by a user from time to time.

The devices and methods also may provide communication and/or messaging capability, which may be useful to communicate additional information to the user including tutorials, patient tracking, system updates, and marketing, sales, and/or promotion messaging. The device also provides means of remote viewing or imaging which may be useful to communicate to a self-administering user the precise location of the tip during use. The proposed solutions also provide the ability to pay for the device and/or operation of the device on a per-treatment basis.

While there are presently a number of proposed solutions to the problem of devices which utilize extracorporeal shock therapy for purposes of treating soft tissue damage, cellulite reduction, or erectile dysfunction, none has been conceived or implemented to permit a simple, inexpensive, robust, home use solution which permit self-applied low intensity shock wave treatment for various parts of the user's body with a form factor, display, information, guidance, tutorials and training, marketing communication and purchase opportunities, viewing angle, timers, annunciators, sound attenuation, and payment options which provide an untrained amateur user with all tools and guidance necessary to properly and safely self-administer treatments which would be optimal for the application.

Low intensity shock wave generation and transfer means embodying the principles of this disclosure solve the problems of a simple, inexpensive, robust, home use solution which permit self-applied low frequency shock wave treatment for various parts of the user's body with a form factor, display, information, guidance, viewing angle, timers, annunciators, and sound attenuation which provide an untrained amateur user with all tools and guidance necessary to properly and safely self-administer treatments for various parts of the user's body as well as including the capability to display and communicate tutorials, patient tracking, system updates, and marketing, sales, and promotion messaging. The several embodiments of the disclosure employ designs, materials, and manufacturing methods which are inexpensive and consistent with current manufacturing practices. The functionality, size, cost, simplicity, ease of use, reliability and robustness of the proposed designs are all advantageous.

Implementations following the principles of this disclosure allow the advantageous modality of a simple, inexpensive, robust, home use solution which permit self-applied low frequency shock wave treatment for various parts of the user's body with a form factor, display, information, guidance, viewing angle, timers, annunciators, and sound attenuation which provide an untrained amateur user with all tools and guidance necessary to effectively and safely self-administer treatments shock wave treatment for various parts of the user's body and have the capability of delivering tutorials, patient tracking, system updates, and marketing, sales, and/or promotion messaging which would be optimal for the application.

FIG. 1 shows a plan view of one embodiment of the device 100 extending between proximal end 102 and distal end 104. Device 100 includes a housing 126 in the form of an elongated, generally cylindrical body which is easily and conveniently grasped in the user's hand in such a manner as to advantageously permit the user to accurately place tip 1 on the desired area of the body to apply treatment. Display 125 is advantageously positioned so as to permit an unobstructed line of site for the viewer from the proximal end 102 toward the distal end 104 during most normal usage. End cap or nose cone 128 is easily accessible and removably attached to housing 126 by any of a variety of conventional means including an internal screw thread, an interrupted thread, a snap lock or any of a variety of mechanical fasteners, so as to facilitate the simple installation, removal, replacement, or switching of tip 110 as required for the selected treatment. In one embodiment, nose cone 128 is secured to housing 126 by an interrupted thread which requires no tools and only a partial rotation to remove and replace. Bar graph segments 173 are readily viewed by the user when the device is positioned and held for use; and annunciator LEDs 172 are also readily seen during use of device 100.

Still referring to FIG. 1, smartphone 151 may be seen to be in proximity to device 100 and may be in communication with the device 100. In at least some examples, smartphone 151 may be wirelessly data connected to device 100 by means of a communication module, for example Bluetooth or any of a variety of other wireless data connection means and protocols, for purposes of wirelessly communicating with device 100. It is through such communication of smartphone 151 with device 100, more specifically with printed circuit board 134 and the electronic components situated thereon including microprocessors and other semiconductors and a memory, that a bi-lateral communication means may be established between device 100 and smartphone 151. This bi-lateral communication means may be advantageously utilized for communication, display, control, monitoring, and/or marketing functions.

Given that smartphone 151 is able to communicate wirelessly with device 100, it may be utilized to perform several functions which are advantageous for the user. First, it may serve as the control panel and information display for device 100. This is advantageous for several reasons. First, smartphone 151 likely has a touch screen and large color display which enable a very high-quality graphical user interface which may variably and preferentially display information and/or controls as needed. Smartphone 151 may also advantageously be placed in a location which is optimal for the user to see displayed information and interact with controls to turn the device 100 on and off, or stop and start operation of the device 100.

Given that smartphone 151 is capable of internet enabled communication, it may be used to provide any of the following: tutorial and coaching information to the user including 'how-to' videos prior to or during use, usage tips; health, diet, exercise, and lifestyle tips to maximize results; and sales and marketing opportunities to purchase consumables, upgrade or purchase additional units, purchase spare parts; and social links to connect the user with user groups, community bulletin boards, and other social media resources including potentially dating sites, clubs, organizations, and groups. Smartphone 151 may also be utilized to keep track of treatments, results, user progress, and provide reminders about upcoming treatments or recommended ancillary treatments or products. Further, smartphone 151 may provide user access to frequently asked question resources and potentially also to live chat or human operators for additional assistance.

In some examples, device 100 may be deployed on parts of the user's body which are difficult to see with direct line of site for example when the device is being used to reduce cellulite on the buttocks or back of the thigh, yet which are important to visually monitor during use, device 100 may be equipped with a camera 174 which may be of a closed circuit, webcam or any of a wide variety of other cameras well known in the art, so located proximal to the nose cone 128 of device 100 by which means it provides a field of view including tip 110 of device 100 and the treatment area of the user, which can communicate the image data with smartphone 151 which displays it, thereby enabling the user to see where tip 110 of device 100 is being placed during use.

In some examples, smartphone 151 is capable of internet enabled communication and e-commerce functions with a remote server, and it may serve as the secure communication, monitoring, and payment portal through which a fundamentally new model of service may be enabled—a 'pay per pulse' or 'pay as you go' model wherein device 100 is sold at a very low cost, or given at no cost to the end user, but will not operate until activated. Activation is accomplished by means of an application or 'app' which is downloaded and installed on the user's smartphone 151, and which by means of secure and/or encrypted wireless communication with device 100 permits the user to purchase by means of e-commerce or any of a wide range of well-known transaction means activation permission for the device 100 which activation permission is quantified by treatment duration or intensity, number of pulses of operation, or duration of use, or by any other delimiting factor deemed necessary or desirable. Once a purchase has been made in-app, the user's smartphone 151 communicates securely with device 100 by means of the aforementioned secure wireless communications link and authorizes device 100 to operate at the user's discretion to the limit of the purchased activation permission. By this means, two of the greatest obstacles to the commercial sale of this device are overcome: first, the initial purchase price, which may be dramatically lower than would be the case for a device which did not require purchase of activation permission which is essentially a means of spreading the total cost of purchase and operation over time; and second, the concern that the device will no perform as promised or will not for any of a variety of reasons be acceptable or desirable for the purchaser and in the event that the device was purchased at full price without the requirement of activation permissions, there is a far greater risk of financial loss for the purchaser if they elect not to utilize the device after purchase. The activation permission model essentially distributes the risk far more favorably for the purchaser.

Still referring to FIG. 1, it may be seen how several of the control and display features including alphanumeric display 125, annunciator LEDs 172, and LED bar graph 173 advantageously communicate critical operational status and tutorial information to the user as follows:

Upon power up by means of on/off switch 159, alphanumeric display 125, annunciator LEDs 172, and LED bar graph 173 are illuminated. This indicates that device 100 has been energized and is ready for use and operation. Given that device 100 is intended for use by a user who most likely has no special training or medical knowledge, one of the principal challenges, which has been met by one of the inventive steps disclosed herein, is the means by which an untrained user may safely and effectively self-administer treatment with the device. The first challenge for the untrained user is to understand which line of travel to follow with tip 110 of device 100. In the instance that device 100 is being used to treat erectile dysfunction, the treatment protocol specifies 5 lines of travel longitudinally along the user's penis. These lines of travel are along the top centerline, and along the upper and lower sides of the penis as most readily communicated by calling them out as positions on a clock face— for example 12 o'clock is the top centerline, 2 o'clock is the upper left side line of travel, etc. To this end, annunciator LEDs 172 are so arranged and oriented on device 100 as to provide a simple and unambiguous guide to the user indicating which line of travel is to be treated, which has already been treated, and which has not yet received treatment. To facilitate the user knowing which line of travel is being called for at each stage of the treatment, annunciator LEDs 172 may exhibit one of 3 states when device 100 is energized. In the unilluminated state, the LED remains off and no color is displayed. This indicates that the corresponding line of travel has not yet been treated. If annunciator LED 172 is illuminated green, this indicates that this particular line of travel is currently being treated, indicating that this is the line of travel upon which tip 110 of device 100 is to be placed. Once treatment along this line of travel has been completed, annunciator LED 172 changes to red illumination color. This indicates that treatment for this line of travel has been completed. To further illustrate the point, upon initial power-up of device 100, all annunciator LEDs 172 are off, except the line of travel which is to receive the first treatment, which will be illuminated green. Upon completion of 4 lines of treatment, 4 annunciator LEDs 172 will be illuminated red, and the annunciator LED 172 indicating the final line of treatment will be illuminated green.

In order that the user has time to place tip 110 of device 100 on the appropriate line of travel and to prepare to administer the treatment, device 100 is energized upon switching on of on/off switch 159 coupled to a power source (e.g., battery or plug), but it does not begin operating or generating energy waves for treatment. Once device 100 is in position, the user presses momentary start button 171 to activate the device 100. Upon activation, device 100 begins emitting sound waves from tip 110, for treating the target treatment area.

Still referring to FIG. 1, it may be plainly seen how LED bar graph 173 is advantageously positioned to be visible to the user during operation of device 100. The function of LED bar graph 173 is to provide the user with visual guidance for the rate of travel of tip 110 of device 100 across the treatment area. Bar graph 173 eliminates the need for the device to be operated by skilled, trained medical professionals. Instead, bar graph 173 allows for operation by an unskilled user, and reduce or eliminate the risk of physical injury as a result of improper use. The single greatest risk to the user is the administration of an excessive number of sound wave pulses to any one area of soft tissue. Low intensity shock wave devices are intended to be in constant motion along a treatment path of travel, rather than remaining in one location for a period of time. A second risk to the user is that of reduced efficacy of treatment because the rate of travel of tip 110 is too fast. To safeguard against both eventualities and to make device 100 more safely and effectively operated and self-deployed by an untrained user, the inventive step of a pacing LED bar graph 173 has been incorporated in device 100 to provide an analogue visual reference guide for the rate of travel of tip 110 along the designated treatment path. The 10 emissive elements of LED bar graph 173 begin all illuminated upon initial energizing of device 100. One LED however, either in position 1 or position 10 will not be steadily illuminated, but will instead be flashing. By this means, the user will know upon which end of the line of travel to place tip 110 and thereby upon which end of the line of travel to begin treatment.

As treatment begins, the user moves tip 110 of device 100 along the line of treatment. The rate of travel is likely something an untrained user has no awareness of and conventional means of quantifying a rate of travel are difficult to comprehend and difficult to translate into operation for an untrained, unskilled user; yet proper rate of travel of tip 110 of device 100 is crucial to the safety and efficacy of the device. To this end, LED bar graph 173 begins decrementing immediately upon treatment initiation once momentary start button 171 has been depressed. Decrementing is accomplished by turning off each successive LED in LED bar graph 173 after one tenth of the treatment time duration for a single line of travel has elapsed. For example, if the duration of treatment for one pass on one line of treatment travel is 10 seconds, one LED of LED bar graph 173 will extinguish illumination each second, in succession. By this means, the user will be able to visually equate the percentage of the line of treatment which has been treated as well as the percentage of the line of treatment remaining to be treated with the percentage of LEDs extinguished and illuminated respectively. For example, the user will readily comprehend that when the first 5 LEDs are extinguished, and the next 5 LEDs remain illuminated, the tip 110 of device 100 should be halfway along the line of treatment, such that the line of treatment will be completed and the tip 110 of device 100 will be at the terminus point of the line of treatment concurrent with the extinguishment of the final LED, number 10. By this means, the user is able to perform a safe and effective treatment based on a proper rate of travel along each line of treatment.

Upon completion of one pass of device 100 along a line of travel of treatment, LED bar graph 173 once again illuminates all emissive elements, with all elements illuminated steadily, except for the last LED which blinks, indicating that this is the end of the line of travel at which the next treatment pass will begin. The LEDs will now begin successively extinguishing, once again providing a proportional visual analog for the user to properly gauge the position and rate of travel of device 100 at any point in the treatment cycle.

Still referring to FIG. 1, we now discuss the function of alphanumeric display 125. Upon initial energization of device 100, alphanumeric display 125 will display the total number of passes required for the first line of treatment travel. In the event that the treatment protocol calls for 10 passes on each line of treatment, alphanumeric display 125 will initially display the number 10. Upon activation of device 100 by pressing momentary start button 171, and the initiation of one pass along the line of treatment travel by the user, alphanumeric display 125 will continue to display the number of passes for the current line of travel, until such time as the device reaches the terminus point of the line of travel as indicated by the extinguishment of all segments of LED bar graph 173, at which point the alphanumeric display 125 will decrement one count, in this case now display "9" indicating that 9 passes remain on this treatment cycle for this line of travel. Alphanumeric display 125 will continue to decrement until the full count of passes per the treatment protocol has been executed. At this time, device 100 will be de-activated, meaning it ceases producing sonic waves, and concurrently the annunciator LED 172 for the just competed line of travel will change in illumination from green to red and the next indicated line of travel annunciator LED 172 will illuminate green indicating that the user should reposition tip 110 of device 100 on the indicated line of travel and prepare to initiate another phase of the treatment. By this means, even the unskilled user may perform a safe and effective treatment with proper positioning of lines of travel, proper rate of travel of device 100 and proper counts for passes along each line of travel. It is anticipated that each of the aforementioned variables including duration of treatment per pass along a line of travel, number and location of lines of travel, rate of travel, and number of passes along each line of travel may be altered or varied depending on the treatment type and patient needs, and may be altered interactively in the case that device 100 is coupled to the internet by means of smartphone or some other means of connectivity well known in the art.

Upon completion of a complete course of treatment comprising the prescribed number of passes along each line of treatment travel for all prescribed lines of treatment travel, the device will go into a sleep mode wherein it will not operate for a prescribed period of time, perhaps 36 hours or 72 hours or 96 hours. The purpose of this timeout function is to prevent over-use by an overly enthusiastic user lacking medical knowledge or training, thereby not understanding that excessive use will not only not yield greater results buy may actually be harmful or dangerous. By this means, yet another inventive step, the untrained user is once again limited to a prescribed course of treatment which is safe and effective.

Alphanumeric display 125 may be utilized to display the number of hours remaining in the time out mode until operation of the device may resume.

A further software resident operating limitation may dictate total operational life of the device wherein after a certain total cumulative number of pulses the unit enters a 'sunset' mode where it will no longer operate. Conversely, it may simply give a visual indication on the alphanumeric display 125 or some such other display that the unit has reached the end of its design life and requires service or replacement. The purpose of this feature is to safeguard against the continued usage of the device beyond the design life, after which the energy signature may be compromised due to the excessive wear or failure of high stress components within the device responsible for generating the shock wave.

Figure 2:
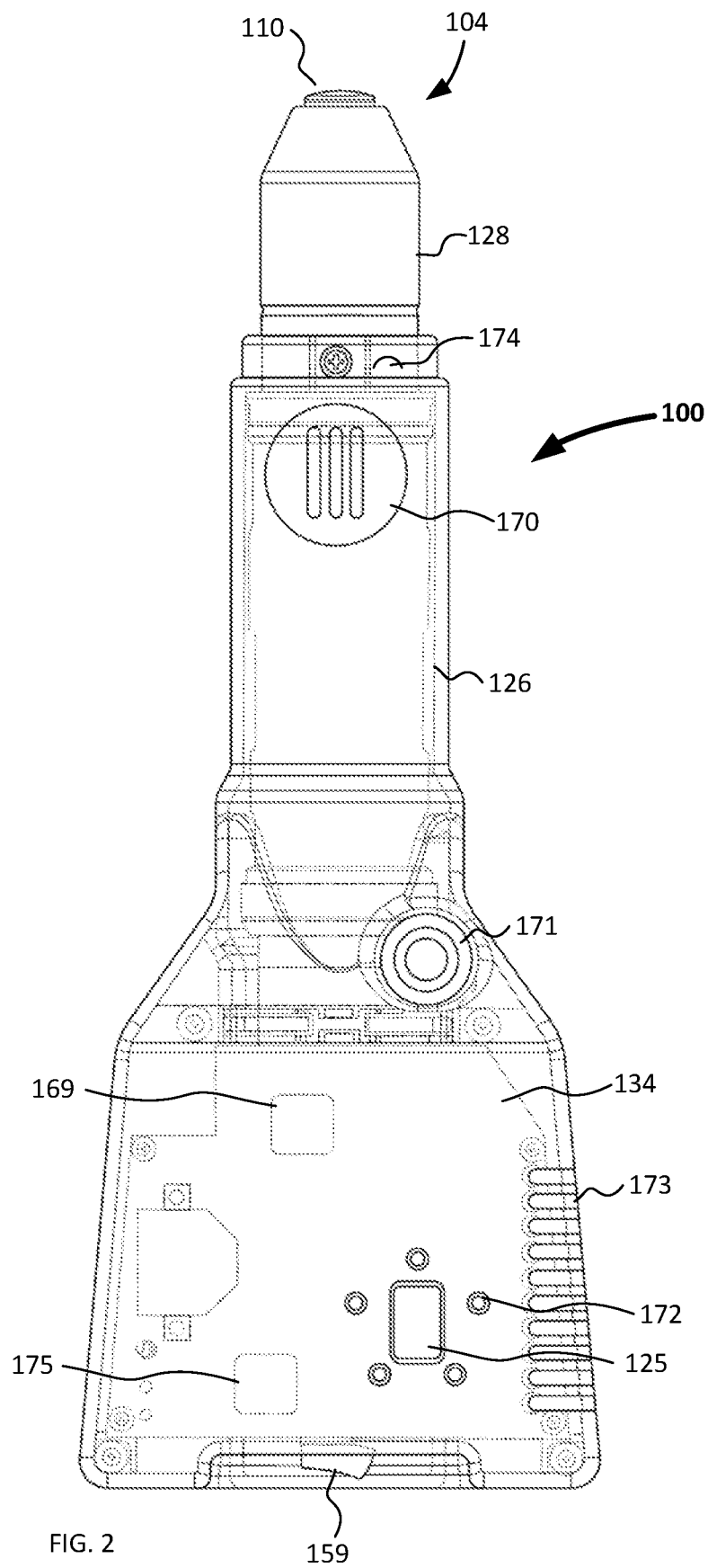
FIG. 2 is a schematic translucent plan view of one embodiment of the disclosure showing major components used to create and administer low frequency shock waves.

Referring now to FIG. 2 which is a translucent plan view of one embodiment of the disclosure, the arrangement of certain major components may be plainly seen including the placement and location of printed circuit board 134 advantageously positioned to support the aforementioned controls and displays, and also incorporating blue tooth communication integrated circuit 175 and audio processor/amplifier 169.

Figure 3:
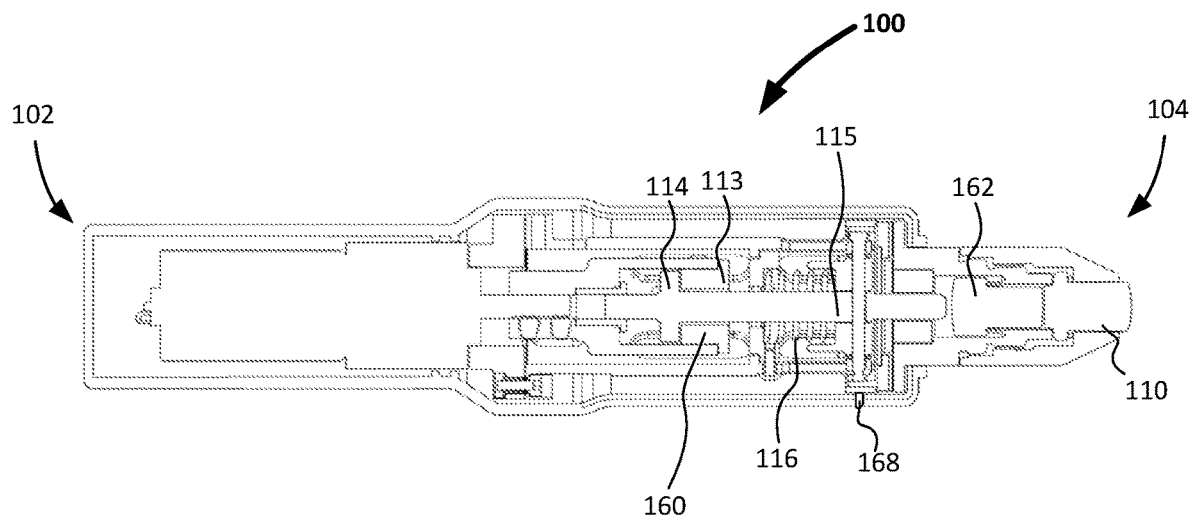
FIG. 3 is a schematic side sectional view of one embodiment of the disclosure.

Referring now to FIG. 3 which is side section view of one embodiment of the device, it may be plainly seen how major components of the assembly are arranged and interact with one another, particularly driveshaft 115, transfer slug 162, and tip 110. In this view it may be seen how compression spring 116 is compressed by cam follower 114 riding the ramps of helical cam 113 until such time as cam follower 114 falls off of cam toe 160 thereby precipitously releasing the stored energy in compression spring 116 which causes driveshaft 115 to rapidly accelerate towards transfer slug 162. Further, it may be understood how driveshaft 115 collides with transfer slug 162 with great velocity and kinetic energy, and as a result of this collision transfer slug 162 collides with tip 110 with similarly great velocity and kinetic energy. These repeated collisions which in the preferred embodiment of device 100 occur 15 times per second create a high decibel sound which may be problematic for users for several reasons. First, the sheer decibel level and frequency of the sound may be painful to listen to and potentially harmful to the hearing of anyone in close proximity, thereby requiring hearing protection during operation of the device 100; and second, in some instances a user desires discretion during use of the device 100 so as not to alert others in close proximity to the fact of their utilization of the device. For both of these reasons it may be desirable to significantly reduce the decibel level of the operation noise created by the device 100.

While certain materials and design practices well known in the art may be employed to attenuate these sounds passively, it may be desirable to further attenuate sound levels beyond that which may be accomplished by such means. To this end, it may be desirable to employ a noise mitigation technique known as active noise cancelling.

Figure 4:
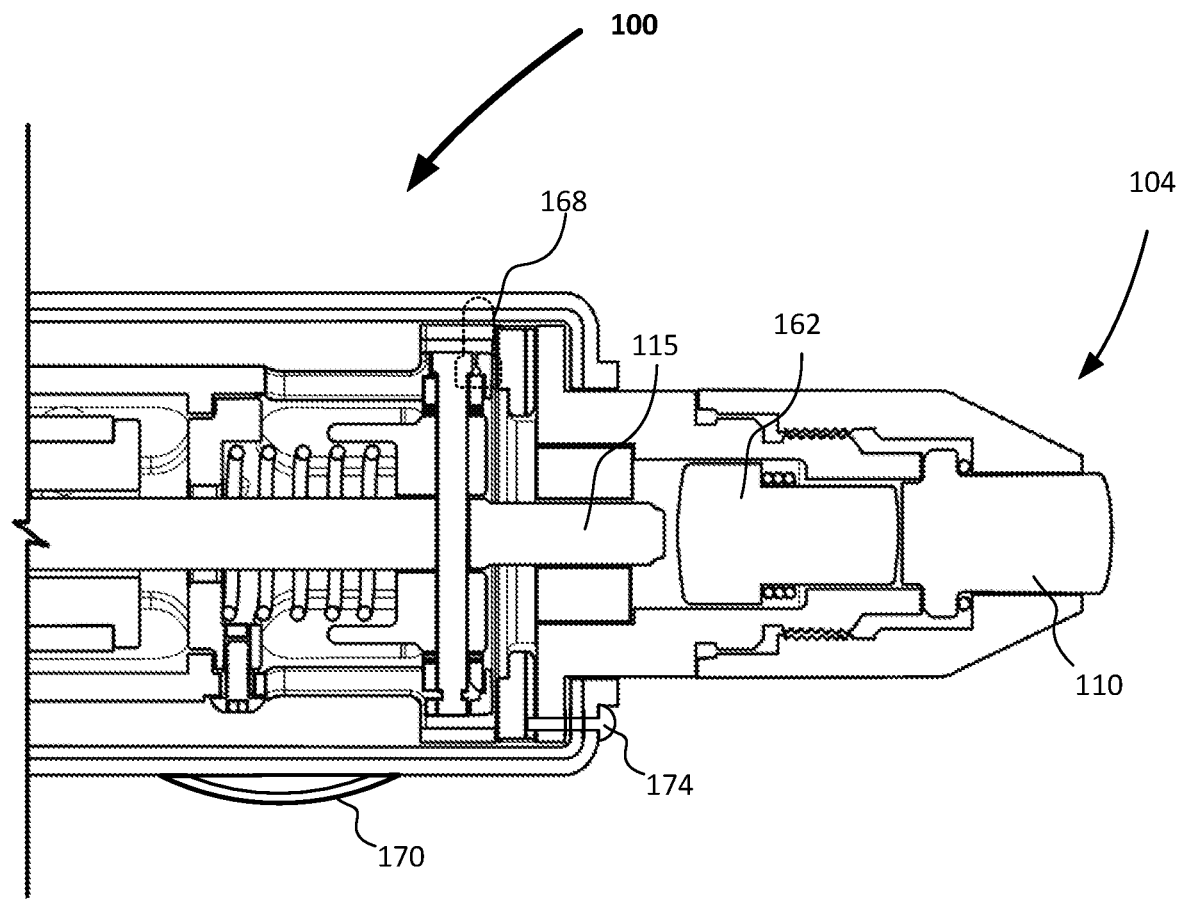
FIG. 4 is a schematic closeup sectional side view of one embodiment of the disclosure.

Referring now to FIG. 4 which is a close up side section view of the proximal end of the preferred embodiment of the device, it may be more plainly seen how driveshaft 115, transfer slug 162 and tip 110 interact with one another and collide inelastically to transfer energy from the initial storage source of compression spring 116 to driveshaft 115, to transfer slug 162, to tip 110 and thereby to the treatment area of the user. Active noise cancellation which is well known in the art has never been applied to a low intensity shock wave device. Such devices are particularly well suited to sound attenuation by active noise cancellation given that active noise cancellation works best in an environment where the objectionable sounds are consistent, fixed, predictable, and occurring at regular intervals—essentially precisely the operating conditions of device 100.

Still referring to FIG. 4, it may be seen how microphone 168 is so positioned and located as to be able to monitor the sound energy created by the collision of driveshaft 115 with transfer slug 162, and with transfer slug 162 and tip 110. The monitored signal is transmitted to audio processor/amplifier 169 on printed circuit board 134, both visible in FIG. 2. Audio processor/amplifier 169 analyzes the signal received from microphone 168 and generates an identical audio signal which is phase shifted one half phase in order to effectively cancel the sound emanating from the device. The amplified phase shifted signal is transmitted to speaker 170 which may be a standard cone and voice coil, piezo electric or any of a variety of other speaker types well known in the art and which may actually be multiple speakers strategically located so as to optimally cancel the offensive original generated noise from device 100, said speaker emitting a phase shifted mimic of the original detected sound which will in large part cancel the overall sound of the device, and by this means render the device much quieter for safe, discreet operation.

It may be seen in these several embodiments of the disclosure that the disclosure overcomes the deficiencies of all previous attempts at solving the problem of device which administers low intensity shock waves to targeted areas of the user's body for treatment of soft tissue damage, cellulite reduction, or erectile dysfunction which is a safe, inexpensive, self-applied, home use solution which does not require a second person to operate, significant medical or anatomical knowledge, special training, and which provide for tutorials, patient tracking, system updates, and marketed, sales, and promotion capabilities, which would be optimal for the application.

In broad embodiment, the present disclosure is a device which administers low frequency shock waves to targeted areas of the user's body for treatment of soft tissue damage, cellulite reduction, or erectile dysfunction which is a safe, inexpensive, self-applied, home use solution which does not require a second person to operate, significant medical or anatomical knowledge, special training, and which provide for tutorials, patient tracking, system updates, and marketing, sales, and promotion capabilities, and reduced noise, which would be optimal for the application.

While the foregoing written description of the disclosure enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure as claimed.

The invention claimed is:

1. A treatment device comprising:
a housing having a longitudinal axis extending between a proximal end and a distal end;
a striking element disposed within the housing and moveable along the longitudinal axis;
a tip disposed adjacent the distal end;
a position indicator for alerting a user to a proper location on the body to be treated, wherein the position indicator includes a plurality of lights, each of the plurality of lights indicating a line of travel along a body part; and
a visual rate indicator that changes over time for guiding the user on an appropriate rate of travel of the tip across a treatment area by indicating a percentage of a treatment line left to be treated.

2. The treatment device of claim 1, wherein the plurality of lights includes five lights corresponding to five lines of travel.

3. The treatment device of claim 1, wherein the plurality of lights are arranged in a circle, each of the plurality of lights corresponds to the location on the body as represented on a clockface.

4. The treatment device of claim 1, wherein each of the plurality of lights includes an LED light capable of signifying three conditions including an untreated condition, an in-treatment condition, and a treated condition.

5. The treatment device of claim 4, wherein each LED light is configured to be unilluminated to signify an untreated condition, to be illuminate green to signify an in-treatment condition, and to illuminate red to signify a treated condition.

6. The treatment device of claim 1, further comprising a display disposed adjacent a distal end of the housing.

7. The treatment device of claim 6, wherein the display is configured to indicate the number of treatments to be performed on each line of travel.

8. The treatment device of claim 1, further comprising a camera disposed on the housing and facing the distal end.

9. The treatment device of claim 1, further comprising a communication module to allow the treatment device to relay data to and from a smartphone.

10. The treatment device of claim 9, wherein the communication module is configured to activate the treatment device for a predetermined period of time.

11. The treatment device of claim 9, wherein the communication module is configured to activate the treatment device for a predetermined number of pulses.

12. A treatment device comprising:
  a housing having a longitudinal axis extending between a proximal end and a distal end;
  a striking element disposed within the housing and moveable along the longitudinal axis;
  a tip disposed adjacent the distal end;
  a processor, wherein the processor is configured to shut off the treatment device for a predetermined period of time after a treatment;
  a memory; and
  a visual rate indicator that changes over time for guiding a user on an appropriate rate of travel of the tip across a treatment area by indicating a percentage of a treatment line remaining to be treated.

13. The treatment device of claim 12, wherein the processor is configured to count a number of pulses.

14. The treatment device of claim 12, wherein the processor is configured to shut off the treatment device for between 72 and 96 hours after a treatment.

15. The treatment device of claim 12, wherein the processor is configured to shut off the treatment device permanently after a predetermined number of treatments.

* * * * *